US010550423B2

(12) United States Patent
Gray

(10) Patent No.: US 10,550,423 B2
(45) Date of Patent: Feb. 4, 2020

(54) MACROMOLECULE DELIVERY TO NANOWELLS

(71) Applicant: IBIS BIOSCIENCES, INC., Carlsbad, CA (US)

(72) Inventor: Phillip N. Gray, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 15/797,982

(22) Filed: Oct. 30, 2017

(65) Prior Publication Data

US 2018/0119205 A1 May 3, 2018

Related U.S. Application Data

(62) Division of application No. 14/369,642, filed as application No. PCT/US2012/072075 on Dec. 28, 2012, now Pat. No. 9,803,231.

(60) Provisional application No. 61/581,508, filed on Dec. 29, 2011.

(51) Int. Cl.
 *C12Q 1/6806* (2018.01)
 *C12Q 1/6869* (2018.01)

(52) U.S. Cl.
 CPC ......... *C12Q 1/6806* (2013.01); *C12Q 1/6869* (2013.01)

(58) Field of Classification Search
 CPC ........... C12Q 2523/303; A61K 47/549; A61K 47/64; B82Y 30/00; B82Y 5/00; G01N 2333/4712; Y10S 977/71; Y10S 977/725
 See application file for complete search history.

(56) References Cited

U.S. PATENT DOCUMENTS

| 5,695,934 | A  | 12/1997 | Brenner |
| 5,714,330 | A  | 2/1998  | Brenner et al. |
| 5,750,341 | A  | 5/1998  | Macevicz |
| 5,830,659 | A  | 11/1998 | Stewart |
| 5,912,148 | A  | 6/1999  | Eggerding |
| 5,976,336 | A  | 11/1999 | Dubrow et al. |
| 6,130,073 | A  | 10/2000 | Eggerding |
| 6,210,891 | B1 | 4/2001  | Nyren et al. |
| 6,258,568 | B1 | 7/2001  | Nyren |
| 6,261,776 | B1 | 7/2001  | Pirrung et al. |
| 6,306,597 | B1 | 10/2001 | Macevicz |

(Continued)

FOREIGN PATENT DOCUMENTS

WO   WO-0018957 A1   4/2000
WO   WO-2006084132 A2   8/2006

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.

(Continued)

*Primary Examiner* — Betty J Forman
(74) *Attorney, Agent, or Firm* — Casimir Jones S.C.; Kirk Hogan

(57) ABSTRACT

Provided herein is technology relating to depositing and/or placing a macromolecule at a desired site for an assay and particularly, but not exclusively, to methods and systems for transporting a macromolecule such as a protein, a nucleic acid, or a protein:nucleic acid complex to an assay site, such as the bottom of a nanopore, a nanowell, or a zero mode waveguide.

4 Claims, 3 Drawing Sheets

(56) References Cited

U.S. PATENT DOCUMENTS

| | | | |
|---|---|---|---|
| 6,432,360 | B1 | 8/2002 | Church |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,329,492 | B2 | 2/2008 | Hardin et al. |
| 7,476,503 | B2 | 1/2009 | Turner et al. |
| 7,482,120 | B2 | 1/2009 | Buzby et al. |
| 7,486,865 | B2 | 2/2009 | Foquet et al. |
| 7,501,245 | B2 | 3/2009 | Quake et al. |
| 7,668,697 | B2 | 2/2010 | Volkov et al. |
| 7,907,800 | B2 | 3/2011 | Foquet et al. |
| 8,153,375 | B2 | 4/2012 | Travers et al. |
| 8,501,405 | B2 | 8/2013 | Korlach et al. |
| 8,795,961 | B2 | 8/2014 | Rank et al. |
| 9,063,156 | B2 | 6/2015 | Korlach et al. |
| 2003/0203929 | A1 | 10/2003 | Ghosh |
| 2005/0130173 | A1 | 6/2005 | Leamon et al. |
| 2008/0176769 | A1 | 7/2008 | Rank et al. |
| 2008/0241951 | A1 | 10/2008 | Battulga et al. |
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2009/0156791 | A1 | 6/2009 | Hiyama et al. |
| 2010/0009872 | A1 | 1/2010 | Eid et al. |
| 2010/0035254 | A1 | 2/2010 | Williams |
| 2010/0076180 | A1 | 3/2010 | Fujita et al. |
| 2010/0081143 | A1 | 4/2010 | Rank et al. |
| 2010/0137143 | A1 | 6/2010 | Rothberg et al. |
| 2010/0144556 | A1* | 6/2010 | Famouri ............ B82Y 5/00 506/30 |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2010/0323912 | A1 | 12/2010 | Korlach et al. |
| 2011/0306039 | A1 | 12/2011 | Chiou et al. |

OTHER PUBLICATIONS

Afshar K., et al., "Dna Binding and Meiotic Chromosomal Localization of the *Drosophila* Nod Kinesin-like Protein," Cell, 1995, vol. 81 (1), pp. 129-138. 0.

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

Bennett S.T., et al., "Toward the 1,000 Dollars Human Genome," Pharmacogenomics, 2005, vol. 6 (4), pp. 373-382.

Berliner E., et al., "Microtubule Movement by a Biotinated Kinesin Bound to Streptavid in-coated Surface," The Journal of Biological Chemistry, 1994, vol. 269 (11), pp. 8610-8615.

Birren B., et al., eds., Genome Analysis—A Laboratory Manual, vol. 1, Cold Spring Harbor Laboratory Press, 1997, Table of Contents.

Bonaccorsi S., et al., "Fine Mapping of Satellite Dna Sequences along the Y Chromosome of *Drosophila melanogaster*: Relationships Between Satellite Sequences and Fertility Factors," Genetics, 1991, vol. 129 (1), pp. 177-189.

Brenner S., et al., "Gene Expression Analysis by Massively Parallel Signature Sequencing (MPSS) on Microbead Arrays," Nature Biotechnology, 2000, vol. 18 (6), pp. 630-634.

Cassimeris L.U., et al., "Dynamic Instability of Microtubules," Bioessays, 1988, vol. 7, pp. 149.

Co-pending U.S. Appl. No. 11/671,956, filed Feb. 6, 2007.

Co-pending U.S. Appl. No. 11/781,166, filed Jul. 20, 2007.

Davis A., et al., "Purification and Biochemical Characterization of Tubulin from the Budding Yeast *Saccharomyces cerevisiae*," Biochemistry, 1993, vol. 32 (34), pp. 8823-8835.

Diez S., et al., "Nanotechnological Applications of Biomolecular Motor Systems," Physics in Canada, 2009, vol. 65 (1), pp. 7-12.

Eid J., et al., "Real-time Dna Sequencing from Single Polymerase Molecules," Science, 2009, vol. 323 (5910), pp. 133-138.

Endow S.A., "The Emerging Kinesin Family of Microtubule Motor Proteins," Trends in Biochemical Sciences, 1991, vol. 16 (6), pp. 221-225.

Foquet M., et al., "Improved Fabrication of Zero-mode Waveguides for Single-molecule Detection," Journal of Applied Physics, 2008, vol. 103.

Goldstein L.S., "The Kinesin Superfamily: Tails of Functional Redundancy," Trends in Cell Biology, 1991, vol. 1 (4), pp. 93-98.

Guydosh N.R., et al., Direct Observation of the Binding State of the Kinesin Head to the Microtubule, Nature, 2009, Retrieved from the Internet: <URL: http://www.stanford.edu/group/blocklab/Guydosh%20Block%20Nature%202009.pdf>.

Hess H., et al., Molecular Shuttles based on Motor Proteins: Active Transport in Synthetic Environments, Department of Bioengineering, Sep. 18, 2001, Retrieved from the Internet: <URL: http://orion.bme.columbia.edu/hess/Hess_Vogel_Molecular_Biotechnology_review.pdf>.

Hoyt M.A., "Cellular Roles of Kinesin and Related Proteins," Current Opinion in Cell Biology, 1994, vol. 6 (1), pp. 63-68.

International Search Report and Written Opinion for Application No. PCT/US2012/072075, dated Apr. 15, 2013, 24 pages.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

Korlach J., et al., "Long, Processive Enzymatic Dna Synthesis Using 100% Dye-labeled Terminal Phosphate-linked Nucleotides," Nucleosides Nucleotides Nucleic Acids, 2008, vol. 27 (9), pp. 1072-1083.

Korten T., et al., "Towards the Application of Cytoskeletal Motor Proteins in Molecular Detection and Diagnostic Devices," Current Opinion in Biotechnology, 2010, vol. 21 (4), pp. 477-488.

Levene M.J., et al., "Zero-mode Waveguides for Single-molecule Analysis at High Concentrations," Science, 2003, vol. 299 (5607), pp. 682-686.

Li M., et al., "*Drosophila* Cytoplasmic Dynein, A Microtubule Motor that is Asymmetrically Localized in the Oocyte," The Journal of Cell Biology, 1994, vol. 126 (6), pp. 1475-1494.

Lin C.T., et al., "Self-contained, Biomolecular Motor-driven Protein Sorting and Concentrating in an Ultrasensitive Microfluidic Chip," Nano Letters, 2008, vol. 8 (4), pp. 1041-1046.

Lundquist P.M., et al., "Parallel Confocal Detection of Single Molecules in Real Time," Optics Letters, 2008, vol. 33 (9), pp. 1026-1028.

MacLean D., et al., "Application of 'next-generation' Sequencing Technologies to Microbial Genetics," Nature Reviews Microbiology, 2009, vol. 7 (4), pp. 287-296.

Malcos J.L., et al., "Engineering Tubulin: Microtubule Functionalization Approaches for Nanoscale Device Applications," Applied Microbiology and Biotechnology, 2011, vol. 90 (1), pp. 1-10.

Margulies M., et al., "Genome Sequencing in Microfabricated High-Density Picolitre Reactors," Nature, 2005, vol. 437 (7057), pp. 376-380.

Mitra R.D., et al., "Fluorescent in Situ Sequencing on Polymerase Colonies," Analytical Biochemistry, 2003, vol. 320 (1), pp. 55-65.

Moore J.D., et al., "Kinesin Proteins: A Phylum of Motors for Microtubule-based Motility," Bioessays, 1996, vol. 18 (3), pp. 207-219.

Morozova O., et al., "Applications of Next-generation Sequencing Technologies in Functional Genomics," Genomics, 2008, vol. 92 (5), pp. 255-264.

(56) References Cited

OTHER PUBLICATIONS

Non-Final Office Action dated Feb. 19, 2016 for U.S. Appl. No. 14/369,642, filed Jun. 27, 2014.
Pennisi E., "Genomics. Semiconductors Inspire New Sequencing Technologies," Science, 2010, vol. 327 (5970), pp. 1190.
Shendure J., et al., "Accurate Multiplex Polony Sequencing of an Evolved Bacterial Genome," Science, 2005, vol. 309 (5741), pp. 1728-1732.
Sodeik B., et al., "Microtubule-mediated Transport of Incoming Herpes Simplex Virus 1 Capsids to the Nucleus," The Journal of Cell Biology, 1997, vol. 136 (5), pp. 1007-1021.
Stewart R.J., et al., "Direction of Microtubule Movement is an intrinsic Property of the Motor Domains of Kinesin Heavy Chain and *Drosophila* Ncd Protein," Proceedings of the National Academy of Sciences of the United States of America, 1993, vol. 90 (11), pp. 5209-5213.
Stewart R.J., et al., "Identification and Partial Characterization of Six Members of the Kinesin Superfamily in *Drosophila*," Proceedings of the National Academy of Sciences of the United States of America, 1991, vol. 88 (19), pp. 8470-8474.
Tokai N., et al., "Kid, a Novel Kinesin-like Dna Binding Protein, is Localized to Chromosomes and the Mitotic Spindle," The Embo Journal, 1996, vol. 15 (3), pp. 457-467.
Tokai-Nishizumi N., et al., "The Chromokinesin Kid is Required for Maintenance of Proper Metaphase Spindle Size," Molecular Biology of the Cell, 2005, vol. 16 (11), pp. 5455-5463.
Uyeda T.Q., et al., "Myosin Step Size. Estimation from Slow Sliding Movement of Actin Over Low Densities of Heavy Meromyosin," Journal of Molecular Biology, 1990, vol. 214 (3), pp. 699-710.
Vale R.D., et al., "Identification of a Novel force-generating Protein, Kinesin, Involved in Microtubule-based Motility," Cell, 1985, vol. 42 (1), pp. 39-50.
Vale R.D., et al., "The Design Plan of Kines in Motors," Annual Review of Cell and Developmental Biology, 1997, vol. 13 (1), pp. 745-777.
Voelkerding K.V., et al., "Next-Generation Sequencing: from Basic Research to Diagnostics," Clinical Chemistry, 2009, vol. 55 (4), pp. 641-658.
Wang S.Z., et al., "Chromokinesin: A DNA-binding, Kinesin-like Nuclear Protein," Journal of Cell Biology, 1995, vol. 128 (5), pp. 761-768.
Yajima J., et al., "The Human Chromokinesin Kid is a Plus End-directed Microtubule-based Motor," The Embo Journal, 2003, vol. 22 (5), pp. 1067-1074.
Yang J.T., et al., "Evidence that the Head of Kinesin is Sufficient for force Generation and Motility in Vitro," Science, 1990, vol. 249 (4964), pp. 42-47.
Ye G.J., et al., "The Herpes Simplex Virus 1 U(I)34 Protein interacts with a Cytoplasmic Dynein Intermediate Chain and Targets Nuclear Membrane," Journal of Virology, 2000, vol. 74 (3), pp. 1355-1363.

\* cited by examiner

MACROMOLECULE DELIVERY TO NANOWELLS

CROSS-REFERENCE TO RELATED APPLICATIONS

The present Application is a divisional of U.S. application Ser. No. 14/369,642 filed Jun. 27, 2014, which is a national phase application under 35 U.S.C. § 371 of PCT International Application No. PCT/US2012/072075, filed on Dec. 28, 2012, which claims priority to U.S. Provisional Application Ser. No. 61/581,508 filed Dec. 29, 2011, the entirety of which is incorporated by reference herein.

STATEMENT REGARDING FEDERALLY SPONSORED RESEARCH OR DEVELOPMENT

This invention was made with government support under HDTRA1-10-C-0080 awarded by Defense Threat Reduction Agency. The government has certain rights in the invention.

FIELD OF INVENTION

Provided herein is technology relating to depositing and/or placing a macromolecule at a desired site for an assay and particularly, but not exclusively, to methods and systems for transporting a macromolecule such as a protein, a nucleic acid, or a protein:nucleic acid complex to an assay site, such as the bottom of a nanopore, a nanowell, or a zero mode waveguide.

BACKGROUND

The massive parallelization of biological assays and realization of single-molecule resolution have yielded profound advances in the ways that biological systems are characterized and monitored and the way in which biological disorders are treated. Assays are able to interrogate thousands of individual molecules simultaneously, often in real time. In particular, the combination of solid state electronics technologies to biological research applications has provided a number of important advances including, e.g., molecular array technology, i.e., DNA arrays (see, e.g., U.S. Pat. No. 6,261,776), microfluidic chip technologies (see e.g., U.S. Pat. No. 5,976,336), chemically sensitive field effect transistors (ChemFETs), and other valuable sensor technologies.

These biochemical and medical assays often rely on the accurate and precise positioning of individual assay components on a molecular scale. Thousands of nanoscale assays are often patterned on a substrate for macro-manipulation, analysis, and data recording. Accordingly, new tools are needed to arrange and construct assay components with accuracy and precision at a molecular resolution.

Components of Molecular Motors

One of the fundamental processes occurring in biological cells is active transport of individual molecules (e.g., a macromolecule such as a protein or a DNA) on a submicrometer scale. The simplest eukaryotic cell contains thousands of components that must be processed, packaged, sorted, and delivered to specific sites at specific times within the cell. These essential transport processes are carried out by motor proteins (e.g., kinesins and dyneins) that travel along microtubules reaching into every corner of the cell. Motor proteins can be conceptualized as biological machines that transduce chemical energy into mechanical forces and motion.

Microtubules, cytoskeletal fibers with a diameter of about 24 nm, have multiple roles in the cell. Bundles of microtubules form cilia and flagella, which are whip-like extensions of the cell membrane that are necessary for sweeping materials across an epithelium and for swimming of sperm, respectively. Marginal bands of microtubules in red blood cells and platelets are important for these cells' pliability. Organelles, membrane vesicles, and proteins are transported in the cell along tracks of microtubules. For example, microtubules run through nerve cell axons, allowing bi-directional transport of materials and membrane vesicles between the cell body and the nerve terminal. Failure to supply the nerve terminal with these vesicles blocks the transmission of neural signals. Microtubules are also critical to chromosomal movement during cell division. Both stable and short-lived populations of microtubules exist in the cell.

Microtubules are polymers of GTP-binding tubulin protein subunits. Each subunit is a heterodimer of alpha- and beta-tubulin, multiple isoforms of which exist. The hydrolysis of GTP is linked to the addition of tubulin subunits at the end of a microtubule. The subunits interact head-to-tail to form protofilaments; the protofilaments interact side-to-side to form a microtubule. A microtubule is polarized, one end ringed with alpha-tubulin (e.g., the "− end") and the other with beta-tubulin (e.g., the "+ end"), and the two ends differ in their rates of assembly. Generally, each microtubule is composed of 13 protofilaments although 11 or 15 protofilament-microtubules are sometimes found. Cilia and flagella contain doublet microtubules.

Methods have been developed for manipulation of microtubules. Microtubules can be routinely reassembled in vitro from tubulin purified from bovine brains. For example, the nucleation, assembly, and disassembly reactions of microtubules have been well characterized in, e.g., L. U. Cassimeris et al., Dynamic Instability of Microtubules, 7 *Bioessays* 149 (1988). More recently, considerable progress has been made toward producing recombinant tubulin in yeast. See A. Davis et al., Purification and Biochemical Characterization of Tubulin from the Budding Yeast *Saccharomyces cerevisiae*, 32 *Biochemistry* 8823 (1993).

The motor protein, kinesin, was discovered in 1985 in squid axoplasm. R. D. Vale et al., Identification of a Novel Force-generating Protein, Kinesin, Involved in Microtubule based Motility, 42 *Cell* 39-50 (1985). It has been discovered that kinesin is just one member of a very large family of motor proteins. E.g., S. A. Endow, The Emerging Kinesin Family of Microtubule Motor Proteins, 16 *Trends Biochem. Sci.* 221 (1991); L. S. B. Goldstein, The Kinesin Superfamily: Tails of Functional Redundancy, 1 *Trends Cell Biol.* 93 (1991); R. J. Stewart et al., Identification and Partial Characterization of Six Members of the Kinesin Superfamily in *Drosophila*. 88 *Proc. Nat'l Acad. Sci. USA* 8470 (1991). Other motor proteins include dynein, e.g., M.-G. Li et al., *Drosophila* Cytoplasmic Dynein, a Microtubule Motor that is Asymmetrically Localized in the Oocyte, 126 *J. Cell Biol.* 1475-93 (1994), and myosin, e.g., T. Q. P. Uyeda et al, 214 *J. Molec. Biol.* 699-710 (1990). Kinesin, dynein, and related proteins move along microtubules, whereas myosin moves along actin filaments.

Kinesins are motor proteins that act on microtubules and that typically move toward the + end of the microtubule. The prototypical kinesin molecule is involved in the transport of membrane-bound vesicles and organelles. This function is particularly important for axonal transport in neurons. Kinesin is also important in all cell types for the transport of vesicles from the Golgi complex to the endoplasmic reticulum. This role is critical for maintaining the identity and functionality of these secretory organelles.

Kinesins define a ubiquitous, conserved family of over 50 proteins that can be classified into at least 8 subfamilies based on primary amino acid sequence, domain structure, velocity of movement, and cellular function. (Reviewed in Moore, J. D. and S. A. Endow (1996) Bioessays 18:207-219; and Hoyt, A. M. (1994) Curr. Opin. Cell Biol. 6:63-68.) The prototypical kinesin molecule is a heterotetramer composed of two heavy polypeptide chains (KHCs) and two light polypeptide chains (KLCs). The KHC subunits are typically referred to as "kinesin." KHC is about 1000 amino acids in length (having a mass of about 120 kDa) and KLC is about 550 amino acids in length (having a mass of about 60 kDa). Two KHCs dimerize to form a rod-shaped molecule with three distinct regions of secondary structure. At one end of the molecule is a globular motor domain that functions in ATP hydrolysis and microtubule binding. Kinesin motor domains are highly conserved and share over 70% identity. Beyond the motor domain is an alpha-helical coiled-coil region that mediates dimerization. At the other end of the molecule is a fan-shaped tail that associates with molecular cargo. The tail is formed by the interaction of the KHC C-termini with the two KLCs.

The kinesin heavy chains comprise three structural domains: (a) an amino-terminal head domain, which contains the sites for ATP and microtubule binding and for motor activity; (b) a middle or stalk domain, which may form an alpha-helical coiled coil that entwines two heavy chains to form a dimer; and (c) a carboxyl-terminal domain, which probably forms a globular tail that interacts with the light chains and possibly with vesicles and organelles. Kinesin and kinesin-like proteins are all related by sequence similarity within an approximately 340-amino acid region of the head domain, but outside of this conserved region they show no sequence similarity.

The motility activity of purified kinesin on microtubules has been demonstrated in vitro. R. D. Vale et al., Identification of a Novel Force-generating Protein, Kinesin, Involved in Microtubule-based Motility, 42 *Cell* 39-50 (1985). Further, full-length kinesin heavy chain and several types of truncated kinesin heavy chain molecules produced in *E. coli* are also capable of generating in vitro microtubule motility. J. T. Yang et al., Evidence that the Head of Kinesin is Sufficient for Force Generation and Motility In Vitro, 249 *Science* 42 (1990); R. J. Stewart et al, Direction of Microtubule Movement is an Intrisic Property of the Motor Domains of Kinesin Heavy Chain and *Drosophila* NCD Protein, 90 *Proc. Nat'l Acad. Sci. USA* 5209-13 (1993). The kinesin motor domain has also been shown to retain motor activity in vitro after genetic fusion to several other proteins including spectrin, J. T. Yang et al., The Head of Kinesin is Sufficient for Force Generation and Motility In Vitro, 249 *Science* 42 (1990), glutathione S-transferase, R. J. Stewart et al., Direction of Microtubule Movement is an Intrinsic Property of the NCD and Kinesin Heavy Chain Motor Domains, 90 *Proc. Nat'l Acad. Sci. USA* 5209 (1993), and biotin carboxyl carrier protein, E. Berliner, Microtubule Movement by a Biotinated Kinesin Bound to a Streptavidincoated Surface, 269 *J. Biol. Chem.* 8610 (1994).

In addition to kinesins, dyneins are also motor proteins that bind to and act on microtubules and typically move toward the −end of the microtubule. Two classes of dyneins, cytosolic and axonemal, have been identified. Cytosolic dyneins are responsible for translocation of materials along cytoplasmic microtubules, for example, for transport from the nerve terminal to the cell body and transport of endocytic vesicles to lysosomes. As well, viruses often take advantage of cytoplasmic dyneins to be transported to the nucleus and establish a successful infection. Sodeik, B. et al. 136 *J. Cell Biol.* 1007-21 (1997). Virion proteins of herpes simplex virus 1, for example, interact with the cytoplasmic dynein intermediate chain. Ye, G. J. et al. 74 *J. Virol.* 1355-63 (2000). Cytoplasmic dyneins are also reported to play a role in mitosis. Axonemal dyneins are responsible for the beating of flagella and cilia. Dynein on one microtubule doublet walks along the adjacent microtubule doublet. This sliding force produces bending that causes the flagellum or cilium to beat. Dyneins have a native mass between 1000 and 2000 kDa and contain either two or three force-producing heads driven by the hydrolysis of ATP. The heads are linked via stalks to a basal domain which is composed of a highly variable number of accessory intermediate and light chains. Cytoplasmic dynein is the largest and most complex of the motor proteins.

Myosins are actin-activated ATPases, found in eukaryotic cells, that couple hydrolysis of ATP with motion. Myosin provides the motor function for muscle contraction and intracellular movements such as phagocytosis and rearrangement of cell contents during mitotic cell division (cytokinesis). The contractile unit of skeletal muscle, termed the sarcomere, consists of highly ordered arrays of thin actin-containing filaments and thick myosin-containing filaments. Crossbridges form between the thick and thin filaments, and the ATP-dependent movement of myosin heads within the thick filaments pulls the thin filaments, shortening the sarcomere and thus the muscle fiber.

Myosins are composed of one or two heavy chains and associated light chains. Myosin heavy chains contain an amino-terminal motor or head domain, a neck that is the site of light-chain binding, and a carboxy-terminal tail domain. The tail domains may associate to form an alpha-helical coiled coil. Conventional myosins, such as those found in muscle tissue, are composed of two myosin heavy-chain subunits, each associated with two light-chain subunits that bind at the neck region and play a regulatory role. Unconventional myosins, believed to function in intracellular motion, may contain either one or two heavy chains and associated light chains. There is evidence for about 25 myosin heavy chain genes in vertebrates, more than half of them unconventional.

Actin is the most abundant intracellular protein in the eukaryotic cell. Actin filaments interact with myosin in muscles and provide a framework to support the plasma membrane and determine cell shape. In muscle cells, thin filaments containing actin slide past thick filaments containing the motor protein myosin during contraction. Microfilaments are the polymerized form of actin and are vital to cell locomotion, cell shape, cell adhesion, cell division, and muscle contraction. Assembly and disassembly of the microfilaments allow cells to change their morphology. Human cells contain six isoforms of actin. The three alpha-actins are found in different kinds of muscle, nonmuscle beta-actin, and nonmuscle gamma-actin are found in nonmuscle cells, and another gamma-actin is found in intestinal smooth muscle cells. G-actin, the monomeric form of actin, polymerizes into polarized, helical F-actin filaments, accompanied by the hydrolysis of ATP to ADP. A family of actin-related proteins exist that are not part of the actin cytoskeleton, but rather associate with microtubules and dynein.

Zero Mode Waveguides

In some assays, molecules are confined in a series, array, or other arrangement of small holes, pores, or wells, for example, a zero mode waveguide (ZMW). ZMW arrays have been applied to a range of biochemical analyses and have found particular usefulness for genetic analysis. ZMWs typically comprise a nanoscale core, well, or opening disposed in an opaque cladding layer that is disposed upon a transparent substrate, e.g., a circular hole in an aluminum cladding film deposited on a clear silica substrate. J. Korlach et al., Selective aluminum passivation for targeted immobilization of single DNA polymerase molecules in zero-mode waveguide nanostructures. 105 *PNAS* 1176-81 (2008). A typical ZMW hole is ~70 nm in diameter and ~100 nm in depth. ZMW technology allows the sensitive analysis of single molecules because, as light travels through a small aperture, the optical field decays exponentially inside the chamber. That is, due to the narrow dimensions of the well, electromagnetic radiation that is of a frequency above a particular cut-off frequency will be prevented from propagating all the way through the core. Notwithstanding the foregoing, the radiation will penetrate a limited distance into the core, providing a very small illuminated volume within the core. By illuminating a very small volume, one can potentially interrogate very small quantities of reagents, including, e.g., single molecule reactions. The observation volume within an illuminated ZMW is ~20 zeptoliters ($20 \times 10^{-21}$ liters). Within this volume, the activity of DNA polymerase incorporating a single nucleotide can be readily detected.

By monitoring reactions at the single molecule level, one can precisely identify and/or monitor a given reaction. The technology is not limited in the types of single molecule interactions that can be observed (e.g., a non-limiting list is protein-protein, protein-DNA, DNA-DNA, DNA-RNA, RNA-RNA, protein-RNA, lipid-lipid, protein-lipid, enzyme-substrate, enzyme-intermediate, enzyme-product, enzyme-metabolite, enzyme-cofactor, enzyme-inhibitor, etc.). In particular, the technology is the basis for a particularly promising field of single molecule DNA sequencing technology that monitors the molecule-by-molecule (e.g., nucleotide-by-nucleotide) synthesis of a DNA strand in a template-dependent fashion by a single polymerase enzyme (e.g., Single Molecule Real Time (SMRT) DNA Sequencing as performed, e.g., by a Pacific Biosciences RS Sequencer (Pacific Biosciences, Menlo Park, Calif.)). See, e.g., U.S. Pat. Nos. 7,476,503; 7,486,865; 7,907,800; and 7,170,050; and U.S. patent application Ser. Nos. 12/553,478, 12/767,673; 12/814,075; 12/413,258; and Ser. No. 12/413,466, each incorporated herein by reference in its entirety for all purposes. See also, Eid, J. et al. 2009. "Real-time DNA sequencing from single polymerase molecules", 323 *Science:* 133-38 (2009); Korlach, J. et al. "Long, processive enzymatic DNA synthesis using 100% dye-labeled terminal phosphate-linked nucleotides", 27 *Nucleosides, Nucleotides & Nucleic Acids:* 1072-82 (2008); Lundquist, P. M. et al., "Parallel confocal detection of single molecules in real time", 33 *Optics Letters:* 1026-28 (2008); Korlach, J. et al., "Selective aluminum passivation for targeted immobilization of single dna polymerase molecules in zero-mode waveguide nanostructures", 105 *Proc Natl Acad Sci USA:* 1176-81 (2008); Foquet, M. et al., "Improved fabrication of zero-mode waveguides for single-molecule detection", 103 *Journal of Applied Physics* (2008); and Levene, M. J. et al. "Zero-mode waveguides for single-molecule analysis at high concentrations", 299 *Science:* 682-86 (2003), each incorporated herein by reference in its entirety for all purposes.

In conventional use, placing components in the wells of the ZMW relies on simple diffusion to deliver components (e.g., macromolecules such as DNA polymerase and/or DNA and/or DNA/DNA polymerase complexes) to the desired site (e.g., the bottom of the ZMW well) in the zero mode waveguides. As a result, a significant amount of the macromolecule (e.g., the DNA polymerase/DNA complex) needs to be added to the ZMWs to achieve a critical mass sufficient enough to drive the diffusion of the complexes into the bottom of the wells. This process is not efficient: e.g., only a fraction of the complexes reaches the desired sites in the wells and incubation times are required to position the assay components in the proper sites. Moreover, extensive incubation times (e.g., 4 or more hours) are required to form the complexes to be delivered to the ZMWs.

SUMMARY

Provided herein is technology for the active transport of assay components (e.g., a macromolecule such as a DNA, DNA polymerase, DNA/DNA polymerase complex, a protein, etc.) to a desired site for an assay (e.g., the bottom of a ZMW well). The technology provides compositions, methods, and systems using actin filaments or microtubules that are bound to the bottom of a zero mode waveguide. The actin filaments or microtubules serve as transport guides for the macromolecules (e.g., the DNA polymerase or DNA polymerase/DNA complex).

These exemplary embodiments are not intended to limit the technology. Indeed, it is intended to be understood that the technology is widely applicable to any instance in which a molecular cargo needs to be transported to a site. Additional embodiments will be apparent to persons skilled in the relevant art based on the teachings contained herein.

Accordingly, provided herein is technology providing methods, compositions, and systems for the delivery of macromolecules to a desired site. In particular, some aspects of the technology provide for a composition for guiding a macromolecule to a site, wherein the composition comprises a transport guide comprising a loading end and a delivery end at the site; a molecular motor that binds to and moves along the transport guide; and a macromolecule comprising a linking domain, wherein the linking domain links the macromolecule to the molecular motor. Some embodiments further provide that an assay is performed at the site, e.g., some embodiments provide that DNA sequencing occurs at the site. In aspects of the technology related to DNA sequencing, the compositions further comprise a phospho-linked nucleotide.

In some embodiments, the composition finds use in delivering a macromolecule to a well, pore, or nanoscale assay site such as a zero mode waveguide. Accordingly, in some embodiments, the site is in a zero mode waveguide and in some embodiments the site is in a nanowell.

Some embodiments of the technology provide that the transport guide is a microtubule and the molecular motor is one or more of a kinesin and a dynein. Various types of kinesins are appropriate for the technology and thus the technology is not limited by the particular embodiments described herein. For example, in some embodiments the kinesin is a chromokinesin (e.g., a KIN N chromokinesin) and in some embodiments other kinesins are provided in the described compositions. In some embodiments, the transport guide is an actin filament and the molecular motor is a myosin.

The technology finds use in the transport of macromolecules, for instance in some embodiments the macromolecule comprises an enzyme (e.g., a DNA polymerase, an RNA polymerase, a reverse transcriptase) and in some embodiments the macromolecule comprises a nucleic acid (e.g., a DNA or an RNA).

In some embodiments, an enzyme/nucleic acid complex is transported to the site and in some embodiments the composition further comprises an enzyme (e.g., a polymerase, e.g., a DNA or an RNA polymerase) at the site. Some embodiments provide compositions further comprising an anchor to maintain the macromolecule at the site.

The technology provides for the attachment, association, linking, binding, etc. of the molecular motor (e.g., the myosin, dynein, kinesin) to the macromolecule. Thus, in some embodiments a composition is provided in which the linking domain mediates a covalent interaction with the molecular motor and in some embodiments the linking domain mediates a non-covalent interaction with the molecular motor. For example, some embodiments provide that the linking domain comprises a myosin binding domain and/or a microtubule associated protein binding domain. Particular embodiments provide that the macromolecule is a DNA comprising a sequence specifically bound by the chromokinesin. Some embodiments comprise other linking domains and/or systems, for example, some embodiments provide a composition further comprising a streptavidin, a biotinylated oligonucleotide, and a linking domain that is a streptavidin binding domain. Such embodiments additionally provide that the biotinylated oligonucleotide is complementary to a library adaptor sequence.

In some embodiments, the transport guide is stabilized, for example, in a composition comprising a phalloidin, and/or a paclitaxel (e.g., a taxol). In some embodiments, the transport guide is disassembled and/or destabilized by a cytochalasin.

Provided herein are compositions related to delivering macromolecules to a site, e.g., to perform a biological assay such as DNA or RNA sequencing. For example, the technology provides embodiments of compositions for delivering a nucleic acid (e.g., a DNA or an RNA), an enzyme (e.g., a DNA polymerase, an RNA polymerase, or a reverse transcriptase), or an enzyme/nucleic acid complex to the bottom of a zero mode waveguide, wherein the composition comprises an actin filament or a microtubule with one end attached to a bottom of a zero mode waveguide well; a myosin, kinesin, or dynein for traveling along the actin filament or microtubule; and a nucleic acid, an enzyme (such as a DNA polymerase, RNA polymerase, or a reverse transcriptase), or an enzyme/DNA complex attached to the myosin, kinesin, or dynein, wherein the myosin, kinesin, or dynein transports the nucleic acid, enzyme, or enzyme/nucleic acid complex to the bottom of the zero mode waveguide well for single-molecule real-time sequencing.

The technology provides for embodiments of methods, e.g., for delivering a macromolecule to a site, wherein the method comprises maintaining an end of a transport guide at the site; providing a molecular motor adapted for binding the transport guide and moving along the transport guide; and linking the macromolecule to the molecular motor. In some embodiments, the macromolecule is delivered to the site for an assay (e.g., an assay is performed at the site). Some embodiments provide that DNA or RNA sequencing occurs at the site, which, in some embodiments further comprise providing a phospholinked nucleotide. Assays and nucleic acid sequencing are performed in some embodiments in a nanopore, nanowell, and, in some embodiments, in a zero-mode waveguide.

In some embodiments, the transport guide is a microtubule and the molecular motor comprises a kinesin and/or a dynein. Particular embodiments provide that the kinesin is a chromokinesin (e.g., a KIN N chromokinesin). An aspect of the technology provides embodiments in which the transport guide is an actin filament and the molecular motor is a myosin.

The methods provided find use in various embodiments of the technology that transport a macromolecule. For example, in some embodiments, the macromolecule comprises an enzyme such as DNA polymerase or reverse transcriptase and in some embodiments the macromolecule comprises a nucleic acid such as DNA or RNA. Some embodiments provide the enzyme at the site.

The transport guide provides for the transport of a macromolecule to a particular site, e.g., for an assay or nucleic acid sequencing. In some embodiments, the methods comprise maintaining the end of the transport guide at the site, e.g., in a method that comprises attaching the end of the transport guide to the site.

Some embodiments provide that the linking comprises providing a covalent interaction of the macromolecule and the molecular motor and some embodiments provide that the linking comprises providing a non-covalent interaction of the macromolecule and the molecular motor. In particular embodiments, the linking comprises providing a domain comprising a myosin binding domain and/or a microtubule associated protein binding domain. For example, in some embodiments, the macromolecule is a DNA comprising a sequence specifically bound by a chromokinesin. In some embodiments, the methods comprise providing a streptavidin, a biotinylated oligonucleotide, and a streptavidin binding domain. In additional embodiments, the biotinylated oligonucleotide is complementary to a library adaptor sequence in the target nucleic acid. Some embodiments of the methods provide that the transport guide is stabilized by providing a member comprising a phalloidin or a paclitaxel. In some embodiments, the transport guide is disassembled and/or destabilized by a cytochalasin.

Provided herein are methods related to delivering macromolecules to a site, e.g., to perform a biological assay and/or nucleic acid sequencing. For example; the technology provides embodiments of methods for delivering a nucleic acid (e.g., a DNA or an RNA), an enzyme (e.g., a DNA polymerase, an RNA polymerase, or a reverse transcriptase), or an enzyme/nucleic acid complex to the bottom of a zero mode waveguide, wherein the method comprises attaching an actin filament or a microtubule to a bottom of a zero mode waveguide well; providing a myosin, kinesin, or dynein for binding and traveling along the actin filament or microtubule; linking an enzyme (e.g., a DNA polymerase, an RNA polymerase, or a reverse transcriptase), a nucleic acid (e.g., a DNA or an RNA), or an enzyme/nucleic acid complex to the myosin, kinesin, or dynein; and transporting the enzyme (e.g., a DNA polymerase, an RNA polymerase, or a reverse transcriptase), the nucleic acid (e.g., a DNA or an RNA), or the enzyme/nucleic acid complex to the bottom of the zero mode waveguide well for single-molecule real-time sequencing.

The methods and compositions provided herein find use in systems for transporting a macromolecule to a site, e.g., embodiments of a system comprising a transport guide (e.g., an actin filament or a microtubule); a molecular motor for transporting the macromolecule along the transport guide; and a linking domain for linking the macromolecule to the molecular motor.

Some embodiments provide a system for sequencing a nucleic acid molecule (e.g., a DNA, RNA, etc.), the system comprising a transport guide comprising an actin filament or a microtubule; a molecular motor for transporting the macromolecule along the transport guide; a linking domain for linking the macromolecule to the molecular motor; and a phospholinked nucleotide. Some embodiments provide that the sequencing occur in a zero mode waveguide and thus the systems according to some embodiments provide a zero mode waveguide. Some embodiments of the systems further comprise an anchor to maintain the macromolecule at the site. The systems comprise a molecular motor, e.g., in some embodiments the systems comprise a kinesin, a dynein, or a myosin.

The technologies provided herein find use in methods for the manufacture of an assay component, for example, a method of manufacturing an assay component, the method comprising attaching one end of a transport guide to a site; linking a macromolecule to a molecular motor; binding the molecular motor to the transport guide; and transporting the macromolecule to the site. The methods find use in manufacturing a component, surface, device, etc. for performing an assay, e.g., a biological assay to measure the interaction of molecules or. Accordingly, in some embodiments, an assay is performed at the site. Moreover, the methods find use in manufacturing a component, surface, device, etc. for performing nucleic acid sequencing. Accordingly, in some embodiments, nucleic acid sequencing occurs at the site. The technologies find use in the manufacture of components comprising structures for performing assays on a molecular scale, for instance a nanowell, a nanopore, or a zero mode waveguide. Thus, in some embodiments, the site is in a zero-mode waveguide and in some embodiments the site is in a nanowell.

It is contemplated that the technologies described herein make use of an appropriate transport guide and molecular motor and it is not to be construed that the technologies are limited to any particular transport guide and/or molecular motor disclosed herein. Embodiments of the technology comprise exemplary methods wherein the transport guide is a microtubule and the molecular motor comprises a kinesin and/or a dynein. In a particular embodiment, the kinesin is a chromokinesin. In other exemplary embodiments, the transport guide is an actin filament and the molecular motor is a myosin. It is to be understood that the technologies are applicable to transport, place, localize, or otherwise position any macromolecule at a site to manufacture an assay component. In some embodiments, the macromolecule comprises an enzyme such as DNA polymerase or reverse transcriptase and in some embodiments the macromolecule comprises a nucleic acid such as a DNA or an RNA. In some embodiments, the methods further comprise placing the enzyme at the site. In some embodiments, the macromolecule is transported to the site and anchored at the site; as such, in some embodiments, the methods provided further comprise anchoring the macromolecule at the site.

One of skill in the art understands that many technologies are available to link molecules and macromolecules. In some embodiments, the linking comprises covalently interacting with the molecular motor and in some embodiments the linking comprises non-covalently interacting with the molecular motor. In particular embodiments, the linking is mediated by a member comprising a myosin binding domain and/or a microtubule associated protein binding domain. In other embodiments, the macromolecule comprises a sequence specifically bound by the chromokinesin. In some embodiments, the linking is mediated by a streptavidin, a biotinylated oligonucleotide, and a streptavidin binding domain. In a specific embodiment, the biotinylated oligonucleotide is complementary to a library adaptor sequence. Embodiments of the technology comprise stabilizing the transport guide with a composition comprising a phalloidin and/or a paclitaxel. In some embodiments, the transport guide is disassembled and/or destabilized by a cytochalasin.

The technology provided herein finds use in methods for delivering a nucleic acid molecule (e.g., a DNA or an RNA), an enzyme (e.g., a DNA polymerase, RNA polymerase, or reverse transcriptase), or an enzyme/nucleic acid complex to the bottom of a zero mode wave guide, wherein the method comprises attaching an end of an actin filament or a microtubule to a bottom of a zero mode waveguide well; linking the nucleic acid molecule (e.g., a DNA or an RNA), the enzyme (e.g., a DNA polymerase, RNA polymerase, or reverse transcriptase), or the enzyme/nucleic acid complex to a myosin, a kinesin, or a dynein; binding the myosin, the kinesin, or the dynein to the actin filament or the microtubule; and transporting the nucleic acid molecule (e.g., a DNA or an RNA), the enzyme (e.g., a DNA polymerase, RNA polymerase, or reverse transcriptase), or the enzyme/ nucleic acid complex to the bottom of the zero mode waveguide, wherein the myosin, the kinesin, or the dynein transports the nucleic acid molecule (e.g., a DNA or an RNA), the enzyme (e.g., a DNA polymerase, RNA polymerase, or reverse transcriptase), or the enzyme/nucleic acid complex to the bottom of the zero mode waveguide well for single-molecule real-time DNA (or RNA) sequencing.

BRIEF DESCRIPTION OF THE DRAWINGS

These and other features, aspects, and advantages of the present technology will become better understood with regard to the following drawings.

DETAILED DESCRIPTION

Figure 1:
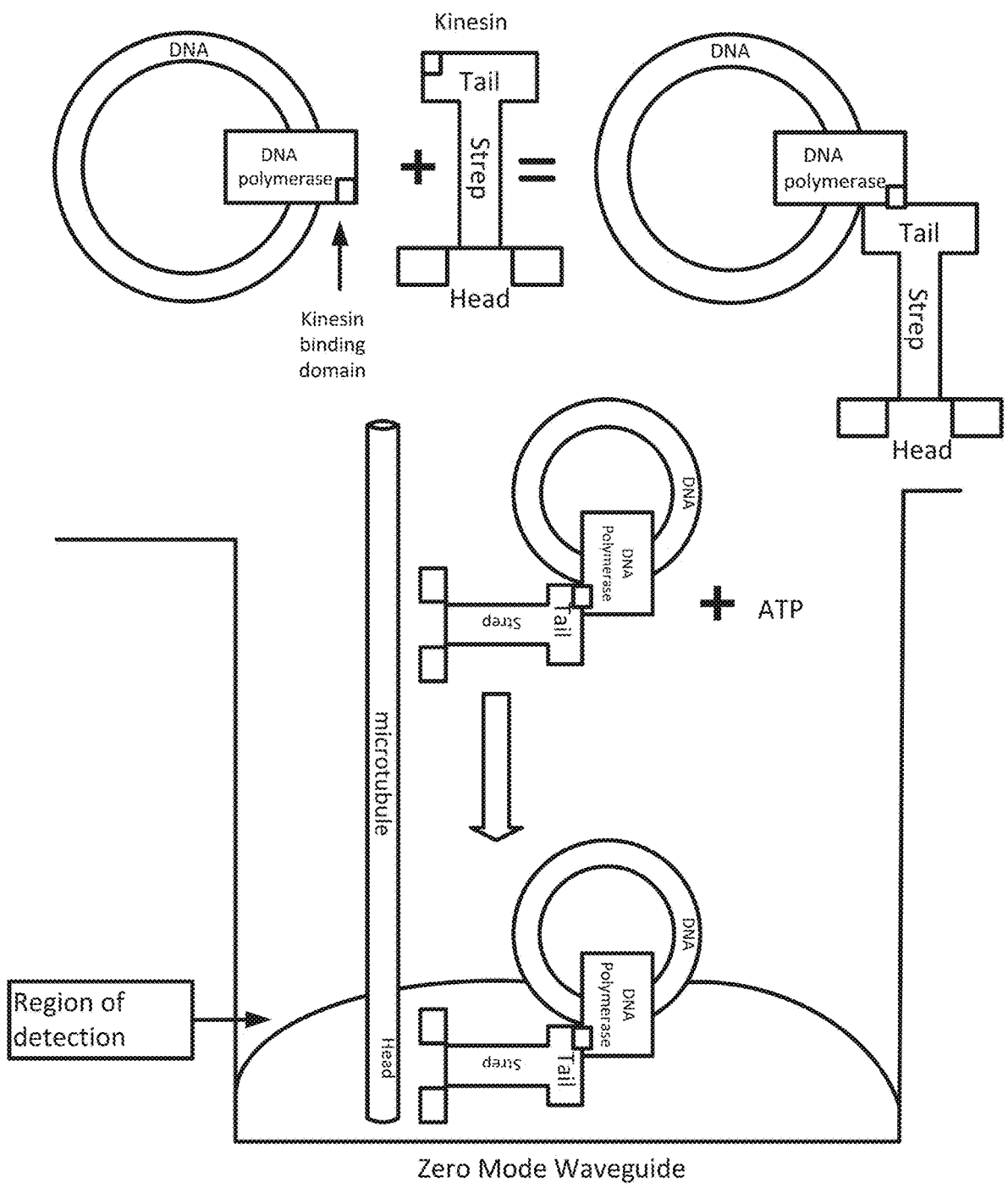
FIG. 1 is a drawing showing an embodiment of the technology comprising a DNA polymerase engineered to contain a kinesin binding domain.

Provided herein is technology for the active transport of assay components (e.g., a macromolecule such as a DNA, DNA polymerase, DNA/DNA polymerase complex, a protein, etc.) to a desired site for an assay (e.g., the bottom of a ZMW well). For example, the technology provides compositions, methods, and systems using actin filaments or microtubules that are bound to the bottom of a zero mode waveguide. The actin filaments or microtubules serve as transport guides for the macromolecules (e.g., the DNA polymerase or DNA polymerase/DNA complex).

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "site" is used to refer to a location in three dimensional space on a molecular scale that is of interest for the technology provided herein (e.g., where a measurement occurs and/or the position of a molecule). In some embodiments, the site is on a surface or on a substrate and in some embodiments the site is in a solution. For example, in some embodiments the site comprises a concentration or collection of molecules (biological molecules or other chemicals) that interact, for example in a biochemical (e.g., enzymatic) reaction (e.g., DNA synthesis). In some embodiments, an interaction of molecules occurs at the site and the interaction is measured, quantified, assessed, and/or otherwise evaluated. In some embodiments, the reactants and/or products consumed and/or produced at the site are measured, quantified, assessed, and/or otherwise evaluated. In some embodiments, the site is the position in space of a single molecule. In some embodiments, the site is the position of a single atom. In some embodiments, the site is at the bottom of a nanowell or zero mode waveguide where a macromolecular interaction or biochemical reaction is monitored.

As used herein, the term "transport guide" is used to refer to a molecular structure that guides the transport of a molecule in three dimensional space, e.g., by a molecular motor. A transport guide provides a substrate for movement of a transporter such as a molecular motor. In some embodiments, a tubulin or actin filament is a transport guide. A transport guide may be thought of as a rail of a molecular train.

As used herein, the term "linking domain" is used to refer to a domain or moiety of a molecule or macromolecule that mediates an association with another interacting partner, e.g., a molecule, macromolecule, or atom. The linking domain may be a native domain of the molecule or macromolecule or may be engineered into the molecule or macromolecule. The linking domain may have other functions in addition to mediating an association with another interacting partner (atom, molecule, macromolecule). In some embodiments, the linking domain interacts directly with another molecule or macromolecule; in some embodiments, the interacting molecules or macromolecules each comprise a linking domain and the association between the molecules or macromolecules is mediated by the interaction of linking domains present on each molecule or macromolecule. In some embodiments, one or more additional molecules or macromolecules may bridge the interaction between a linking domain and a molecule or macromolecule or between the linking domains of one or more molecules or macromolecules. For example, in some embodiments one interacting partner comprises a linking domain that is a streptavidin and the other interacting partner comprises a linking domain that is a biotin. In some embodiments, one linking domain is a streptavidin binding protein, another linking domain is a biotin moiety, and the interaction between the two is mediated by a bridging streptavidin. Additional examples are, in some embodiments, linking domains comprising a DNA-binding domain. For example, a chromokinesin contains both a kinesin motor-like domain and a DNA-binding domain (e.g., a basic-leucine zipper). Accordingly, a chromokinesin (e.g., a KIN N chromokinesin) binds a specific DNA sequence. For example, *Drosophilia* NOD binds the AATAT repeats of the 1.672 satellite DNA (S. Bonaccorsi and A. Lohe. "Fine Mapping of Satellite DNA Sequences along the Y Chromosome of *Drosophila melanogaster*: Relationships between Satellite Sequences and Fertility Factors". 1991 *Genetics* 129(1): 177-89). Human KID binds to cerb2 promoter sequences (Tokai et al., "Kid, a novel kinesin-like DNA binding protein, is localized to chromosomes and the mitotic spindle" 1996 *EMBO J* 15(3): 457-67). See also Afshar et al., "DNA binding and meiotic chromosomal localization of the *Drosophila* nod kinesin-like protein" 1995 *Cell* 81(1): 129-38, all of which are incorporated herein by reference in their entireties.

Specific protein-protein interactions can be used to for linking domains, e.g., antibody-antigen or antibody-epitope, myosin binding domain-myosin, and other specific binding partners known in the art of molecular biology. In some embodiments, the interactions or associations are mediated by a covalent link (e.g., a chemical bond) and in some embodiments the interactions or associations are mediated by a noncovalent link or binding.

As used herein, the term "molecular motor" refers to a molecule, macromolecule, or molecular assembly that utilizes chemical energy to generate mechanical force.

As used herein, a "phospholinked nucleotide" is a nucleotide having a label (e.g., a fluor or dye) attached to a phosphate (e.g., the terminal phosphate, e.g., the terminal phosphate of the NTP triphosphate chain). Upon incorporation of the labeled phospholinked nucleotide into the growing synthesized DNA molecule, the label (e.g., the flour or dye) is cleaved from the NTP.

As used herein, an "anchor" is a molecule or macromolecule that reversibly or irreversibly attaches, immobilizes, localizes, or associates a molecule, macromolecule, or atom to a surface or substrate.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule, but is intended to include other forms such as "portions", "fragments", "variants", and "mutants" as defined below. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (e.g., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include transmembrane domains and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kbp on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

Embodiments of the Technology

In some embodiments, the technology comprises a polymerase (e.g., a DNA polymerase) or other enzyme engineered to contain either a myosin binding domain, which binds the myosin protein, or a microtubule associated protein binding domain, which binds kinesin or dynein, or any other binding domain associated with a transport guide molecule. In some embodiments, a polymerase/nucleic acid complex is formed from an engineered polymerase and a nucleic acid molecule, and then the polymerase/nucleic acid complex is incubated with the appropriate motor protein (e.g., myosin if using actin filaments; kinesin or dynein if using microtubules) for binding. The polymerase/nucleic acid/motor protein complex is then added to the ZMW where it binds and travels down the actin filament or microtubule to the bottom of the well. Motor proteins are known to travel in only one direction: For example, kinesin proteins travel to the positive (+) end of microtubules and dyneins travel to the negative (−) end of microtubules. In embodiments wherein kinesin is used, the positive end of the microtubule is anchored in the bottom of the ZMW and kinesin carries the cargo (DNA polymerase/DNA complex) to the bottom of the well. In embodiments wherein dynein is used, the negative end of the microtubule is anchored in the bottom of the ZMW and dynein carries the cargo (DNA polymerase/DNA complex) to the bottom of the well.

In another aspect of the technology, ZMWs are pretreated with polymerase under conditions that maximize polymerase binding to the well (e.g., ZMWs are incubated with polymerase under optimal conditions for binding for a time sufficient for binding). Microtubules or actin filaments are anchored to the bottom of the ZMWs. Chromokinesins, a specific type of kinesin motor protein that binds specific DNA sequences (see, e.g., Yajima J, E, et al. (2003). "The human chromokinesin Kid is a plus end-directed microtubule-based motor". 22 *EMBO J.*: 1067-74 (2003); Tokai-Nishizumi N, et al. "The chromokinesin Kid is required for maintenance of proper metaphase spindle size" 16 *Mol. Biol. Cell* 5455-63 (2006)), are incubated with DNA libraries that contain the chromokinesin binding sequences (these sequences are incorporated into the library adaptor sequences). The chromokinesin/DNA complexes are then loaded onto the ZMWs containing the microtubules and DNA polymerase. The chromokinesin/DNA complex travels down the microtubule, delivering the complex to the DNA polymerase at the bottom of the well.

In related aspects of the technology, ZMWs are pretreated with polymerase under conditions that maximize polymerase binding to the well (e.g., ZMWs are incubated with polymerase under optimal conditions for binding for a time sufficient for binding). Microtubules or actin filaments are anchored to the bottom of the ZMWs. Kinesin, dynein, or myosin is engineered to contain a linking domain (e.g., a binding domain, e.g., such as a streptavidin binding domain) and incubated with a molecule or molecules that mediate linking a nucleic acid such as a DNA to the kinesin, dynein, or myosin. For example, the kinesin, dynein, or myosin comprisisg a streptavidin binding domain is incubated with streptavidin and a biotinylated oligonucleotide that is complementary to a generic adaptor sequence used to make a DNA library (e.g., each DNA of the library comprises the adaptor sequence). The adaptor sequence is single stranded and binds the complementary oligonucleotide attached to the motor protein (e.g., myosin, kinesin, or dynein). The DNA/oligonucleotide-motor protein complex is loaded onto the ZMW containing a microtubule or actin filament and the previously attached polymerase. The motor protein attaches to the microtubule or the actin filament and transports the DNA library molecule to the bottom of the ZMW where the polymerase is located. The polymerase binds the primed template and sequencing begins.

Actin filaments and microtubules are dynamic structures comprising subunits that can be stabilized with chemical compounds. In some embodiments, actin filaments are stabilized with phalloidins, which bind actin filaments and prevent depolymerization. In some embodiments, microtubules are stabilized with paclitaxel, which has been shown to provide microtubules that are stabilized for times of approximately a week. After delivery, some embodiments provide that the actin filament or microtubule structures are disrupted using compounds such as cytochalasin, leaving only the polymerase/nucleic acid complex in the well of the ZMW. Or, the structure is left intact in some embodiments to anchor the polymerase/nucleic complex in the desired site.

Cytochalasins are fungal metabolites that have the ability to bind to actin filaments and block polymerization and the elongation of actin. Actin microfilaments have been widely studied using cytochalasins. Due to their chemical nature, cytochalasins can help researchers understand the importance of actin in various biological processes. The use of cytochalasins has allowed researchers to understand actin polymerization, cell motility, ruffling, cell division, contraction, and cell stiffness. The use of cytochalasins has been so important to understanding cytoskeletal movement and many other biological processes, researchers have created two synthetic cytochalasins. Paclitaxel is a mitotic inhibitor that was isolated from the bark of the Pacific yew tree, *Taxus brevifolia*, from which its original name "taxol" was derived. When it was developed commercially, the generic name was changed to paclitaxel and the commercial compound was sold under the trademark TAXOL. In this formulation, paclitaxel is dissolved in Cremophor EL and ethanol, as a delivery agent. A newer formulation, in which paclitaxel is bound to albumin, is sold under the trademark ABRAXANE. Paclitaxel stabilizes microtubules and as a result interferes with the normal breakdown of microtubules during cell division. Together with docetaxel, it forms the drug category of the taxanes. It was the subject of a notable total synthesis. Phalloidin is one of a group of toxins from the death cap (*Amanita phalloides*) known as phallotoxins. Phalloidin binds F-actin, preventing actin depolymerization.

The technology finds use in DNA sequencing, e.g., single molecule sequencing. Single molecule sequencing systems, e.g., as developed by Pacific Biosciences are described in Voelkerding et al., 55 *Clinical Chem:* 641-58, 2009; MacLean et al., 7 *Nature Rev. Microbiol.*: 287-96; and in U.S. Pat. Nos. 7,170,050; 7,302,146; 7,313,308; and 7,476,503; all of which are herein incorporated by reference. This technology utilizes reaction wells 50-100 nm in diameter and encompassing a reaction volume of approximately 20 zeptoliters ($10^{-21}$ liters). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the technology finds use for the single molecule real time (SMRT) DNA sequencing methods using zero-mode waveguides (ZMWs) developed by Pacific Biosciences or similar methods. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospho-linked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

While particular embodiments are described herein in reference to particular DNA sequencing methods such as Single Molecule Real Time DNA sequencing as implemented by technologies developed by Pacific Biosciences, the technology of delivering a molecule or macromolecule (e.g., a polymerase or DNA) to a site finds use in other sequencing technologies.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695, 934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, technologies of Oxford Nanopore Technologies Ltd., technologies of Life Technologies/Ion Torrent, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences and emerging platforms commercialized by VisiGen and Pacific Biosciences.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Other embodiments provide for the delivery of a molecule or macromolecule to a site for an assay. Assays for which the technology finds use are, e.g., an ELISA or other immunoassay, array assays (nucleic acid or protein detection microarrays), etc.

Although the disclosure herein refers to certain illustrated embodiments, it is to be understood that these embodiments are presented by way of example and not by way of limitation.

EXAMPLES

Example 1

Embodiments of the technology comprise a DNA polymerase engineered to contain a kinesin binding domain as depicted in FIG. 1. The engineered DNA polymerase is complexed with a DNA that is to be sequenced. The DNA polymerase/DNA is complexed with a kinesin and the DNA polymerase/DNA/kinesin complex is loaded into the zero mode waveguide. Upon the addition of ATP, the kinesin motor travels down the microtubule to the bottom of the zero mode waveguide, in the desired site for sequencing. The DNA polymerase is anchored in the well either by remaining connected to the kinesin or by another interaction such as a streptavidin-biotin interaction used as an anchor.

Example 2

Figure 2:
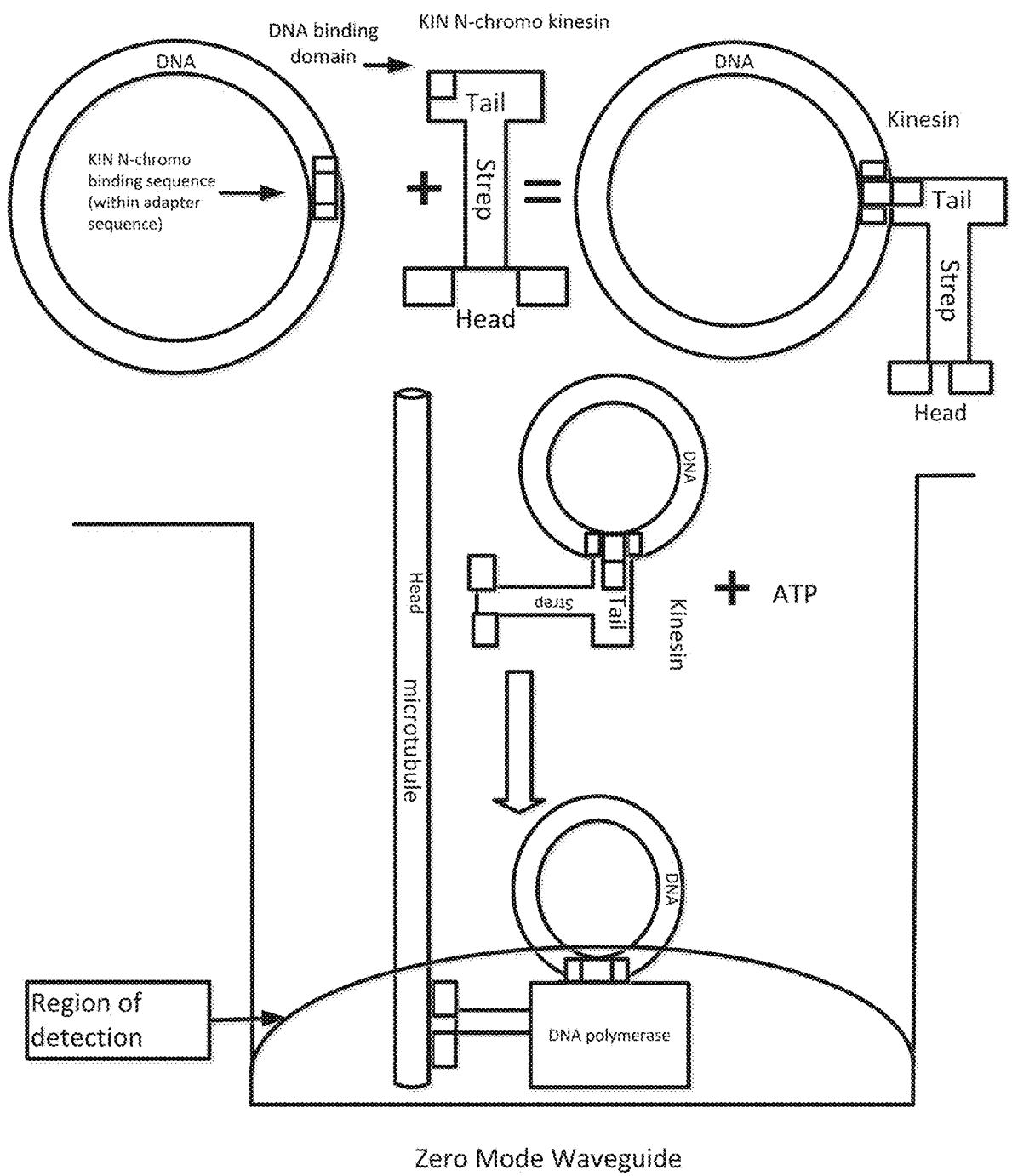
FIG. 2 is a drawing showing an embodiment of the technology comprising a DNA adaptor engineered to contain a chromokinesin binding sequence.

Embodiments of the technology comprise use of a chromokinesin (e.g., a KIN N chromokinesin) as depicted in FIG. 2. DNA libraries are constructed to contain a chromokinesin binding sequence in an adapter. DNA is incubated with the chromokinesin to form a chromokinesin/DNA complex. The chromokinesin/DNA complex is loaded onto a zero mode waveguide, which has been preloaded with immobilized DNA polymerase at the bottom of the well. Upon the addition of ATP, the chromokinesin motor protein travels down the microtubule to the bottom of the zero mode waveguide. The DNA is delivered to the immobilized DNA polymerase. The microtubule and chromokinesin/DNA complex is disrupted, freeing the DNA to bind the polymerase.

Example 3

Figure 3:
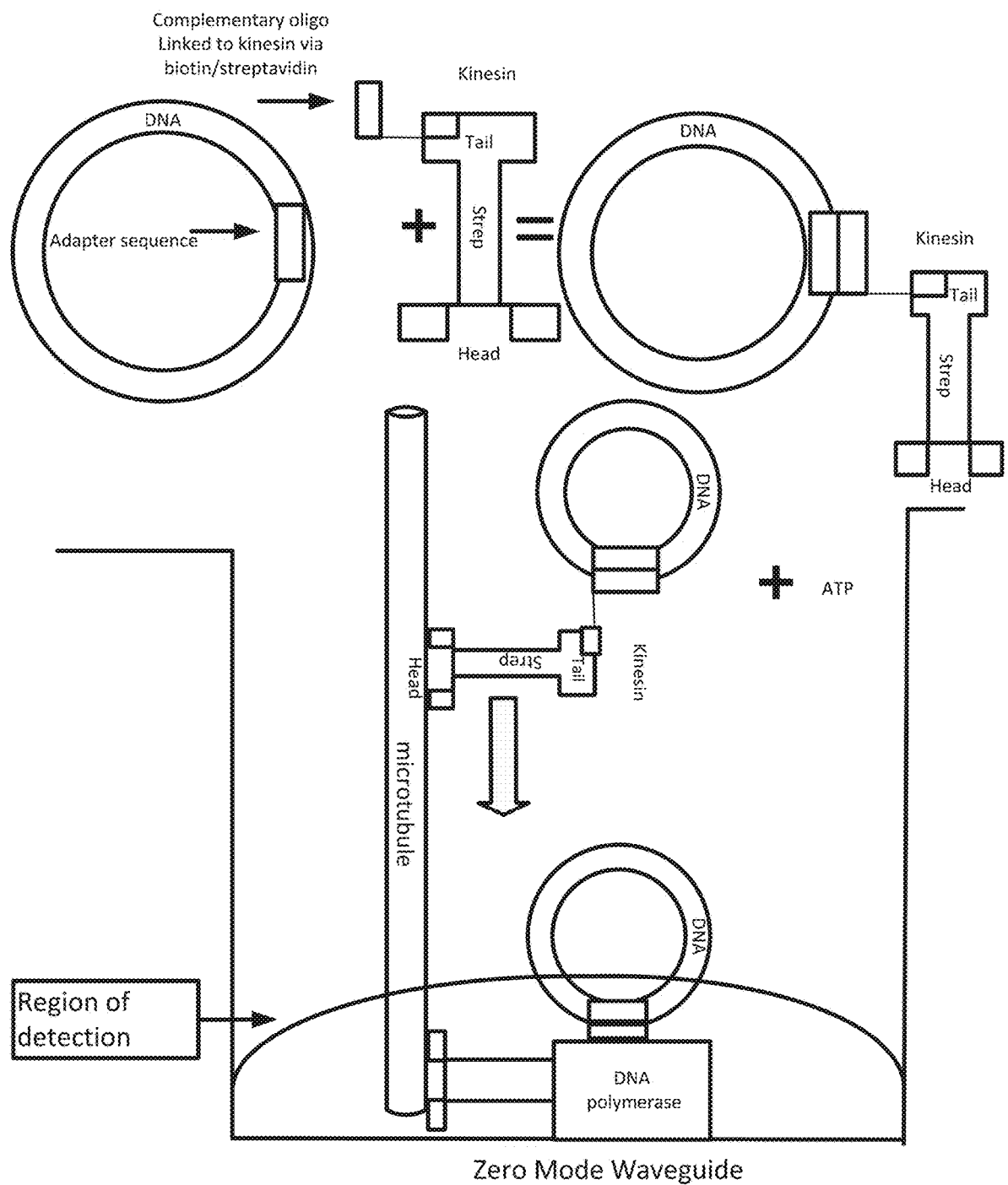
FIG. 3 is a drawing showing an embodiment of the technology comprising a kinesin covalently linked to an oligonucleotide that is complementary to a library adaptor sequence.

Embodiments of the technology comprise use of a kinesin engineered to contain a streptavidin binding domain as depicted in FIG. 3. Kinesin is incubated with streptavidin and a biotinylated oligonucleotide that is complementary to the adaptor sequence of the DNA library. The DNA/kinesin complex is formed via oligonucleotide/adaptor sequence binding. The DNA/kinesin complex is loaded into the zero mode waveguide, which has been preloaded with immobilized DNA polymerase at the bottom of the well. Upon the addition of ATP, the kinesin motor protein travels down the microtubule to the bottom of the zero mode waveguide. The DNA is delivered to the immobilized DNA polymerase. Sequencing can begin on the primed DNA template.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, genomics, biochemistry, medical science, materials science, or related fields are intended to be within the scope of the following claims.

I claim:

1. A system for transporting a macromolecule, the system comprising:
   a) a transport guide comprising an actin filament or a microtubule with one end attached to a bottom of a zero mode wave guide well or nanowell;
   b) a molecular motor for transporting the macromolecule along the transport guide wherein said molecular motor is a myosin, kinesin, or dynein; and
   c) a linking domain linking the macromolecule to the molecular motor wherein said macromolecule is a DNA, a DNA polymerase or a DNA polymerase/DNA complex attached to said molecular motor, said molecular motor is configured to transport said DNA, said DNA polymerase or said DNA polymerase/DNA complex to said bottom of a zero mode wave guide well or nanowell.

2. The system of claim 1 further comprising a phospho-linked nucleotide at said zero mode waveguide or nanowell.

3. The system of claim 1 further comprising an anchor to maintain the macromolecule at said zero mode wave guide well or nanowell.

4. The system of claim 1 wherein said linking domain is selected from the group consisting of a myosin binding domain and a microtubule associated protein binding domain.

* * * * *